(12) United States Patent
Diamond

(10) Patent No.: US 6,168,578 B1
(45) Date of Patent: Jan. 2, 2001

(54) PORTABLE KIDNEY DIALYSIS SYSTEM

(76) Inventor: Melvin Diamond, 1006 Laurel Lake Dr., Ball Ground, GA (US) 30107

( * ) Notice: Under 35 U.S.C. 154(b), the term of this patent shall be extended for 0 days.

(21) Appl. No.: 09/252,106

(22) Filed: Feb. 18, 1999

(51) Int. Cl.[7] .......................... A61M 1/00; A61M 37/00; A61M 5/32; B01D 61/00; C02F 1/44

(52) U.S. Cl. .................. 604/29; 604/5.01; 604/31; 604/179; 604/345; 604/4.01; 210/645; 2/312

(58) Field of Search .............. 604/4–5, 31, 27–29, 604/179, 317, 322–23, 326–28, 332, 335, 345, 353; 210/645–47; 2/69.5, 300, 311–12, 318–19, 321–22, 336, 338; 224/148.1–148.2, 148.4, 660, 667

(56) References Cited

U.S. PATENT DOCUMENTS

| | | | |
|---|---|---|---|
| 3,884,808 | * | 5/1975 | Scott ................................. 210/109 |
| 4,316,466 | * | 2/1982 | Babb .................................. 604/31 |
| 5,284,470 | * | 2/1994 | Beltz ................................... 604/4 |
| 5,728,070 | * | 3/1998 | Walker et al. ...................... 604/179 |
| 5,873,853 | * | 2/1999 | Keilman et al. ..................... 604/67 |
| 5,944,684 | * | 8/1999 | Roberts et al. ...................... 604/5 |

* cited by examiner

Primary Examiner—William E. Kamm
Assistant Examiner—Patricia Bianco

(57) ABSTRACT

A portable kidney dialysis system device is provided including a belt with a drain bag mounted thereon. A pump is also mounted on the belt and coupled between a user and the drain bag. The pump is adapted to pump fluid from the user to the drain bag upon the receipt of a drain signal. Further provided is a pressure switch for detecting when the drain bag is full. A control mechanism serves for transmitting the drain signal to the pump only when the means fails to detect that the drain bag is full.

7 Claims, 3 Drawing Sheets

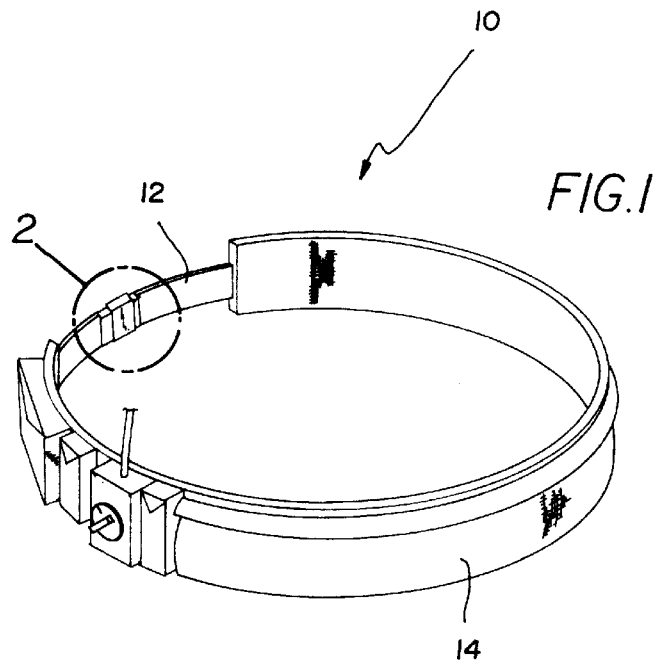
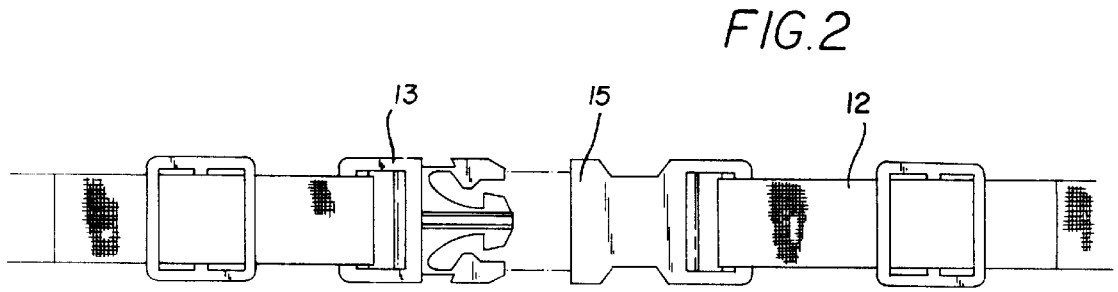

PORTABLE KIDNEY DIALYSIS SYSTEM

BACKGROUND OF THE INVENTION

1. Field of the Invention

The present invention relates to dialysis machines and more particularly pertains to a new portable kidney dialysis system for automatically conducting kidney dialysis with a belt mounted unit.

2. Description of the Prior Art

The use of dialysis machines is known in the prior art. More specifically, dialysis machines heretofore devised and utilized are known to consist basically of familiar, expected and obvious structural configurations, notwithstanding the myriad of designs encompassed by the crowded prior art which have been developed for the fulfillment of countless objectives and requirements.

Known prior art dialysis machines include U. S. Pat. No. 4,765,907; U.S. Pat. No. 5,425,719; U.S. Pat. No. 4,443,333; U.S. Pat. No. 4,180,460; U.S. Pat. Des. No. 308,249; and U.S. Pat. No. 3,955,867.

In these respects, the portable kidney dialysis system according to the present invention substantially departs from the conventional concepts and designs of the prior art, and in so doing provides an apparatus primarily developed for the purpose of automatically conducting kidney dialysis with a belt mounted unit.

SUMMARY OF THE INVENTION

In view of the foregoing disadvantages inherent in the known types of dialysis machines now present in the prior art, the present invention provides a new portable kidney dialysis system construction wherein the same can be utilized for automatically conducting kidney dialysis with a belt mounted unit.

The general purpose of the present invention, which will be described subsequently in greater detail, is to provide a new portable kidney dialysis system apparatus and method which has many of the advantages of the dialysis machines mentioned heretofore and many novel features that result in a new portable kidney dialysis system which is not anticipated, rendered obvious, suggested, or even implied by any of the prior art dialysis machines, either alone or in any combination thereof.

To attain this, the present invention generally comprises a belt with an adjustable length. The belt includes a pair of free ends having a male and female couples attached thereto, respectively. The couples serve for securing the belt on a user. FIGS. 1 & 3 show a drain bag pocket mounted on an outer surface of the belt. The drain bag pocket extends along ¾ of a length of the belt at a rear extent thereof. The drain bag pocket includes a lid integrally coupled to a top edge of the belt with a pile fastener mounted thereon. The pile fastener is adapted for releasably coupling with a pile fastener mounted on a front face of the drain pocket along an entire length thereof. Next provided is a drain bag having a length equal to ¾ that of the belt and a width equal to that of the belt. The drain bag has an end with a flexible tube coupled thereto and extending therefrom. As shown in FIG. 4, the flexible tube terminates with a couple including a rigid tube with a pair of gripping ears extending radially therefrom. Further extending from the couple is a pair of diametrically opposed coupling protrusions. Mounted on an outer surface of the belt adjacent to an end of the drain bag pocket is a pump. A first flexible tube is coupled to the pump and extends within a body of a user. Also coupled to the pump is a second flexible tube terminating with a couple. The couple of the second flexible tube includes a rigid tube with a pair of gripping ears extending radially therefrom and a pair of diametrically opposed coupling slots formed in an inner surface thereof. As such, the present couple is adapted for coupling with the couple of the drain bag and that of a fill bag which is filled with fluid. In use, the pump is adapted to pump fluid from the first flexible tube to the second flexible tube only upon the receipt of a drain signal. Further, the pump serves to pump fluid from the second flexible tube to the first flexible tube only upon the receipt of a fill signal. Mounted within the second flexible tube is a pressure sensor for providing a full signal only upon the detection of a pressure exceeding a predetermined amount. Associated therewith is a flow sensor which is also mounted within the second flexible tube. The flow sensor is adapted for providing a flow signal only upon the detection of a flow of fluid. As shown in FIG. 5, an audio means is included for generating an audible signal only upon the actuation thereof. Finally, control means is mounted on the outer surface of the belt and connected between the pump, the pressure sensor, the flow sensor, audio means, a timer and a manual switch. In use, the control means has a first mode for when the drain bag is connected to the second flexible tube of the pump. In such mode, the drain signal is transmitted for a predetermined amount of time to the motor intermittently at predetermined intervals for filling the drain bag with fluid from the body of the user. Upon the receipt of the flow signal, the pump ceases intermittent transmission of the drain signal and continuously transmits the drain signal until the receipt of either the full signal or the lack of receipt of the flow signal. For alerting the user, the control means only actuates the audio means upon receipt of the full signal. When the drain bag is full, the control means further has a second mode for when the second flexible tube of the pump is connected to the fill bag. It should be noted that the control means only operates in the second mode upon the closing of the manual switch by the user via the rotation of the dial shown in FIG. 5. In the second mode, the control means is adapted for transmitting the fill signal to the pump thereby inserting fluid from the fill bag within the body of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new portable kidney dialysis system apparatus and method which has many of the advantages of the dialysis machines mentioned heretofore and many novel features that result in a new portable kidney dialysis system which is not anticipated, rendered obvious, suggested, or even implied by any of the prior art dialysis machines, either alone or in any combination thereof.

It is another object of the present invention to provide a new portable kidney dialysis system which may be easily and efficiently manufactured and marketed.

It is a further object of the present invention to provide a new portable kidney dialysis system which is of a durable and reliable construction.

An even further object of the present invention is to provide a new portable kidney dialysis system which is susceptible of a low cost of manufacture with regard to both materials and labor, and which accordingly is then susceptible of low prices of sale to the consuming public, thereby making such portable kidney dialysis system economically available to the buying public.

Still yet another object of the present invention is to provide a new portable kidney dialysis system which provides in the apparatuses and methods of the prior art some of the advantages thereof, while simultaneously overcoming some of the disadvantages normally associated therewith.

Still another object of the present invention is to provide a new portable kidney dialysis system for automatically conducting kidney dialysis with a belt mounted unit.

Even still another object of the present invention is to provide a new portable kidney dialysis system that includes a belt with a drain bag mounted thereon. A pump is also mounted on the belt and coupled between a user and the drain bag. The pump is adapted to pump fluid from the user to the drain bag upon the receipt of a drain signal. Further provided is a pressure switch for detecting when the drain bag is full. A control mechanism serves for transmitting the drain signal to the pump only when the means fails to detect that the drain bag is full.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new portable kidney dialysis system according to the present invention.

FIG. 2 is a front view of the belt of the present invention.

DESCRIPTION OF THE PREFERRED EMBODIMENT

Figure 3:
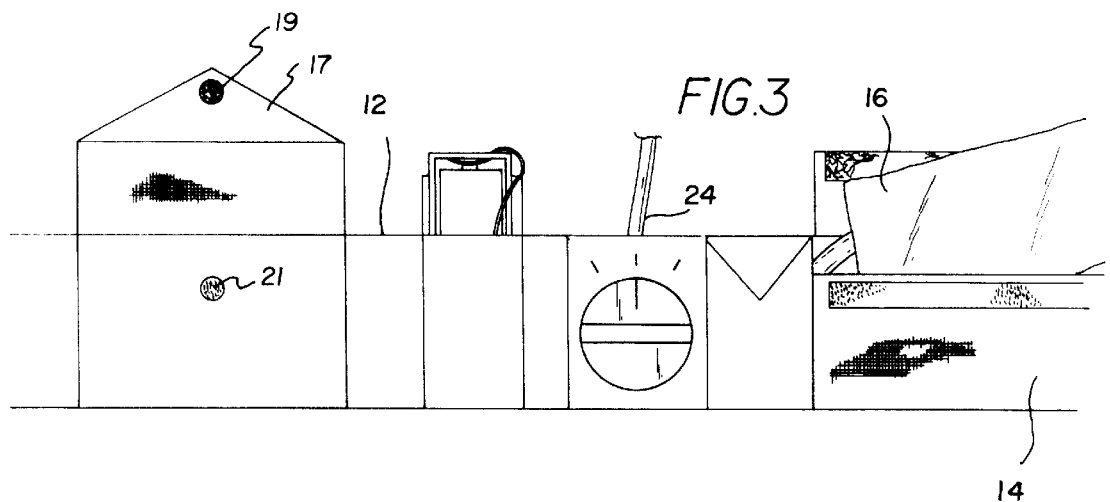
FIG. 3 is a front view of the various components mounted to the belt of the present invention.

With reference now to the drawings, and in particular to FIGS. 1 through 5 thereof, a new portable kidney dialysis system embodying the principles and concepts of the present invention and generally designated by the reference numeral 10 will be described.

The present invention, designated as numeral 10, includes a belt 12 with an adjustable length. The belt includes a pair of free ends having a male 13 and female 15 couples attached thereto, respectively. The couples serve for securing the belt on a user.

FIGS. 1 & 3 show a drain bag pocket 14 mounted on an outer surface of the belt. The drain bag pocket extends along ¾ of a length of the belt at a rear extent thereof. The drain bag pocket includes a lid 17 integrally coupled to a top edge of the belt with a pile fastener 19 mounted thereon. The pile fastener is adapted for releasably coupling with a pile fastener 21 mounted on a front face of the drain pocket along an entire length thereof.

Figure 4:
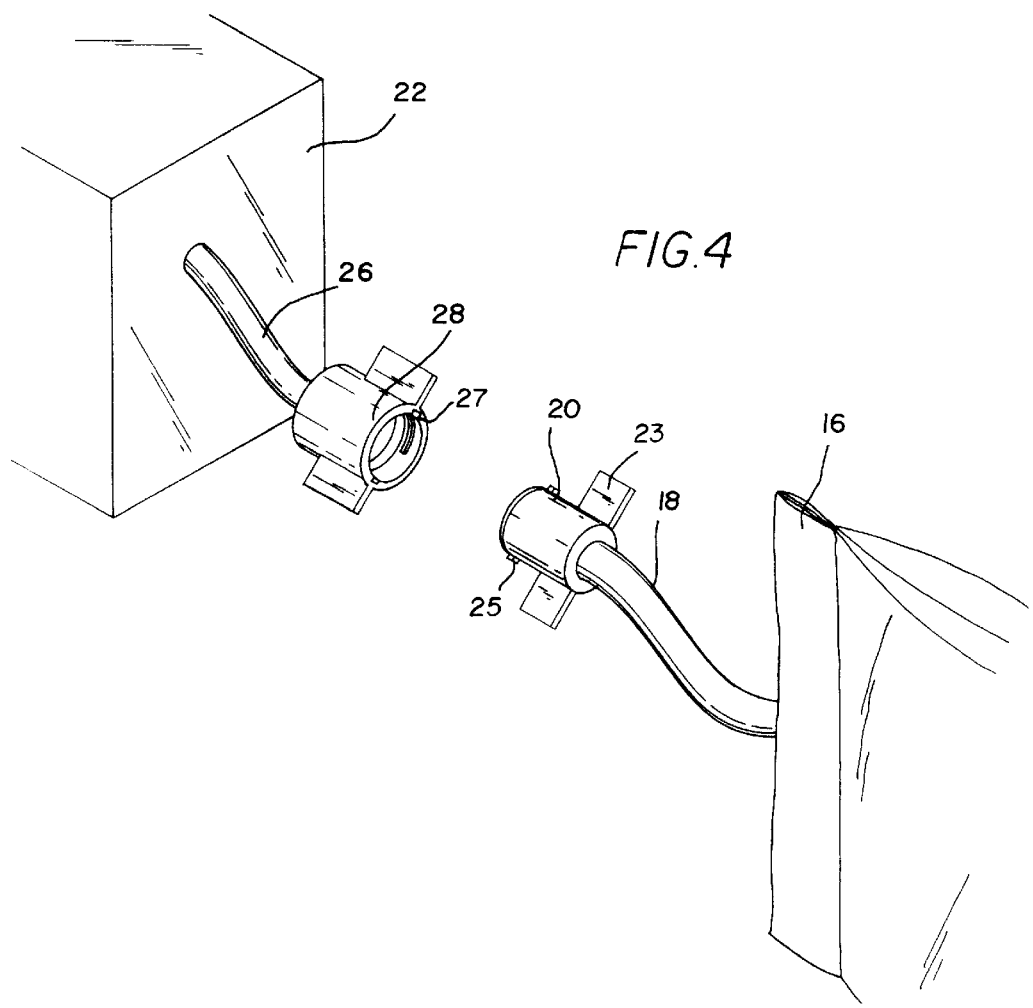
FIG. 4 is a perspective view of the drain bag, pump and second flexible tube of the present invention.

Next provided is a drain bag 16 having a length equal to ¾ that of the belt and a width equal to that of the belt. The drain bag has an end with a flexible tube 18 coupled thereto and extending therefrom. As shown in FIG. 4, the flexible tube terminates with a couple 20 including a rigid tube with a pair of gripping ears 23 extending radially therefrom. Further extending from the couple is a pair of diametrically opposed coupling protrusions 25.

Mounted on an outer surface of the belt adjacent to an end of the drain bag pocket is a battery operated pump 22. The pump is preferably a reverse polarity pump. A first flexible tube 24, or catheter, is coupled to the pump and extends within a body of a user. Also coupled to the pump is a second flexible tube 26 terminating with a couple 28. The couple of the second flexible tube includes a rigid tube with a pair of gripping ears extending radially therefrom and a pair of diametrically opposed coupling slots 27 formed in an inner surface thereof. As such, the present couple is adapted for coupling with the couple of the drain bag and that of an unillustrated fill bag which is filled with fluid. The fill bag may either be stored separate the belt or thereon.

In use, the pump is adapted to pump fluid from the first flexible tube to the second flexible tube only upon the receipt of a drain signal. Further, the pump serves to pump fluid from the second flexible tube to the first flexible tube only upon the receipt of a fill signal. Its should be noted that each of the various components including the battery and pump are situated within corresponding pockets formed in the belt.

Figure 5:
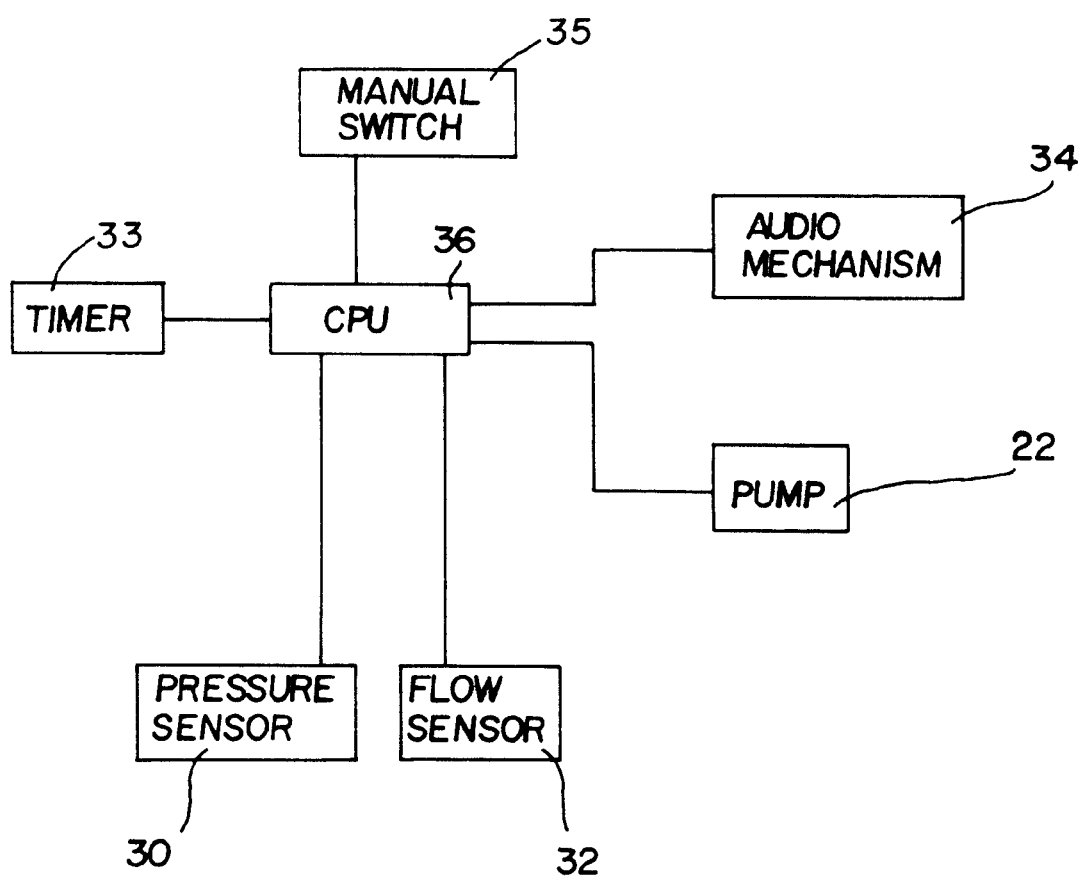
FIG. 5 is a schematic diagram of the present invention.

Mounted within the second flexible tube is a pressure sensor 30 for providing a full signal only upon the detection of a pressure exceeding a predetermined amount. It should be noted that the pressure within the drain bag will be the same as that in the tube. Associated therewith is a flow sensor 32 which is also mounted within the second flexible tube. The flow sensor is adapted for providing a flow signal only upon the detection of a flow of fluid. It should be noted that such sensors are commonly known and commercially available. As shown in FIG. 5, an audio means 34, in the form of a piezoelectric buzzer or the like, is included for generating an audible signal only upon the actuation thereof.

Finally, control means 36, in the form of a microprocessor or the like, is mounted on the outer surface of the belt and connected between the pump, the pressure sensor, the flow sensor, the audio means, a timer 33 and a manual switch 35. In use, the control means has a first mode for when the drain bag is connected to the second flexible tube of the pump. In such mode, the drain signal is transmitted for a predetermined amount of time to the motor intermittently at predetermined intervals for filling the drain bag with fluid from the body of the user. In the preferred embodiment, the intervals are about 1 minute and the predetermined amount of time is enough to generate a fluid flow if it is present.

Upon the receipt of the flow signal, the pump ceases intermittent transmission of the drain signal and continuously transmits the drain signal until the receipt of either the full signal or the lack of receipt of the flow signal. For alerting the user when the drain bag is full, the control means only actuates the audio means upon receipt of the full signal.

When the drain bag is full, the control means further has a second mode for when the second flexible tube of the pump is connected to the fill bag. It should be noted that the control means only operates in the second mode upon the closing of the manual switch by the user via the rotation of the dial shown in FIG. 5. In the second mode, the control means is adapted for transmitting the fill signal to the pump thereby inserting fluid from the fill bag within the body of the user.

By this structure, the present invention allows automatic pumping of fluid from the user to the drain bag which is mounted on the belt. Such fluid flow is effected only when the fluid is available from the user. When the drain bag is full, a sensor alerts the user to replace the drain bag with a fill bag full of cleansing fluid which is pumped into the body only when the manual switch is closed via the dial. After this procedure is complete, a new drain bag may be coupled to the pump and mounted on the belt such that the operation may repeat itself. In the preferred embodiment, the manual switch or dial has three orientation, a first orientation for affording the first mode of operation, a second orientation for affording the second mode of operation and a third orientation for precluding operation.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A portable kidney dialysis system device comprising, in combination:

a belt;

a drain bag mounted on the belt and having an interior;

a pump mounted on the belt, a first tube being coupled to an inlet of the pump, the first tube being adapted for insertion into a body of a user, a second tube being coupled to an outlet of the pump and being in fluid communication with the interior of the drain bag, the pump being adapted to pump fluid from the first tube to the drain bag upon the receipt of a drain signal;

a motor for operating the pump;

detecting means operatively connected to the drain bag for detecting when the drain bag is full;

a timer; and a control mechanism operatively coupled to the motor, the detecting means, and the timer, the control mechanism transmitting the drain signal to the pump only when the detecting means fails to detect that the drain bag is full, the control mechanism having a first mode for when the second tube is connected to the drain bag wherein the drain signal is transmitted for a predetermined amount of time to the motor intermittently at predetermined intervals for filling the drain bag with fluid from the body of the user.

2. A portable kidney dialysis system device as set forth in claims 1 wherein an outlet of the pump is further interchangeably coupleable to a fill bag when not connected to the drain bag and operation of the motor is reversible through a switch for the purpose of reversing the pumping direction of fluid to move fluid from the fill bag to the user.

3. A portable kidney dialysis system device as set forth in claim 2 wherein the pump is interchangeably releasably attachable to both the fill bag and drain bag via a similar tube releasably fluidly connectable to the outlet of the pump.

4. A portable kidney dialysis system device as set forth in claim 1 additionally comprising an audio means operatively connected to the detecting means for generating an audible signal when the drain bag is full.

5. A portable kidney dialysis system device as set forth in claim 1 wherein the control means transmits the drain signal to the pump only when fluid is available to be pumped from the user.

6. A portable kidney dialysis system device as set forth in claim 1 wherein the detecting means includes a pressure switch.

7. A portable kidney dialysis system device comprising, in combination:

a belt with an adjustable length and including a pair of free ends having a male and female couples attached thereto, respectively, for securing the belt on a user;

a drain bag pocket mounted on an outer surface of the belt and extending along ¾ of a length of the belt at a rear extent thereof, the drain bag pocket including a lid integrally coupled to a top edge of the belt with a pile fastener mounted thereon for releasably coupling with a pile fastener mounted on a front face of the drain pocket along an entire length thereof;

a drain bag having a length equal to ¾ that of the belt and a width equal to that of the belt, the drain bag having an end with a flexible tube coupled thereto and extending therefrom thus terminating with a couple including a rigid tube with a pair of gripping ears extending radially therefrom and a pair of diametrically opposed coupling protrusions;

a pump mounted on an outer surface of the belt adjacent to an end of the drain bag pocket, a first flexible tube being coupled to an inlet of the pump and being adapted for insertion into a body of a user, and a second flexible tube coupled to an outlet of the pump and terminating with a couple including a rigid tube with a pair of gripping ears extending radially therefrom and a pair of diametrically opposed coupling slots formed in an inner surface thereof for coupling with the couple of the drain bag and that of a fill bag which is filled with fluid, wherein the pump is adapted to pump fluid from the first flexible tube to the second flexible tube only upon the receipt of a drain signal and further pump fluid from the second flexible tube to the first flexible tube only upon the receipt of a fill signal;

a pressure sensor mounted in the second flexible tube for providing a full signal only upon the detection of a pressure exceeding a predetermined amount;

a flow sensor mounted in the second flexible tube for providing a flow signal only upon the detection of a flow of fluid;

audio means for generating an audible signal only upon the actuation of the audio means;

a timer; and control means mounted on the outer surface of the belt and connected between the pump, the pressure sensor, the flow sensor, audio means, the timer and a manual switch, the control means having a first mode for when the drain bag connected to the second flexible tube of the pump wherein the drain signal is transmitted for a predetermined amount of time to the motor intermittently at predetermined intervals for filling the drain bag with fluid from the body of the user, whereby upon the receipt of the flow signal, the drain signal is continuously transmitted until the receipt of either the full signal or the lack of receipt of the flow signal, wherein the control means only actuates the audio means upon receipt of the full signal, the control means further having a second mode only upon the closing of the manual switch for when the second flexible tube of the pump is connected to the fill bag for transmitting the fill signal to the pump for inserting fluid from the fill bag within the body of the user.

\* \* \* \* \*